United States Patent [19]
Hilgers et al.

[11] Patent Number: 5,131,843
[45] Date of Patent: Jul. 21, 1992

[54] ORTHODONTIC ARCHWIRE

[75] Inventors: James J. Hilgers, Escondido; Farrokh Farzin-Nia, Inglewood, both of Calif.

[73] Assignee: Ormco Corporation, Glendora, Calif.

[21] Appl. No.: 696,100

[22] Filed: May 6, 1991

[51] Int. Cl.$^5$ ............................................. A61C 3/00
[52] U.S. Cl. ................................................. 433/20
[58] Field of Search .......................................... 433/20

[56] References Cited

U.S. PATENT DOCUMENTS

| | | | |
|---|---|---|---|
| 3,178,822 | 4/1965 | Fogel et al. | 433/20 |
| 4,050,158 | 9/1977 | Brader | 433/20 |
| 4,097,993 | 7/1978 | Andrews | 433/20 |
| 4,197,643 | 4/1980 | Burstone et al. | 433/20 |
| 4,268,250 | 5/1981 | Reeve | 433/20 |
| 4,490,112 | 12/1984 | Tanaka et al. | 433/20 |
| 4,818,226 | 4/1989 | Berendt et al. | 433/20 |

Primary Examiner—John J. Wilson
Attorney, Agent, or Firm—Wood, Herron & Evans

[57] ABSTRACT

An orthodonic archwire and method of making same. The archwire through a unique combination of physical and material properties can be activated for providing a variety of teeth corrective forces simultaneously. The archwire is provided with a pair of loop structures substantially equidistant from the center line of the arch form., The posterior sections of the archwire are curved in two directions so as to provide both toe in forces, for rotation of the posterior teeth, and forces for extrusion of the posterior teeth and bite opening. The method of manufacturing the archwire is such that substantially no residual torque is present in the finally formed archwire.

29 Claims, 3 Drawing Sheets

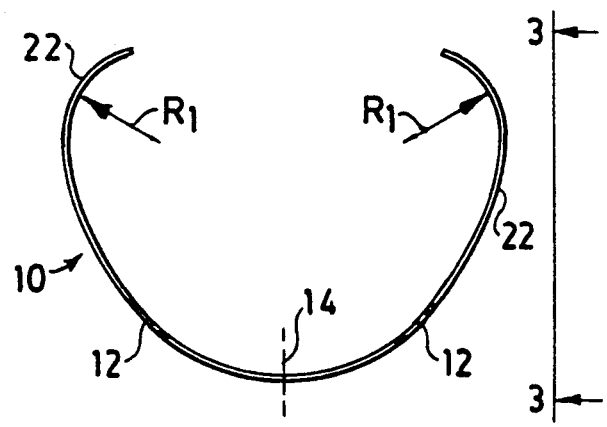
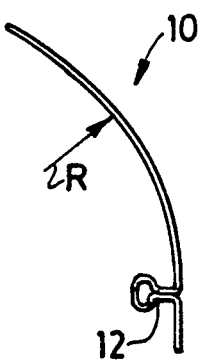
FIG.1          FIG.3
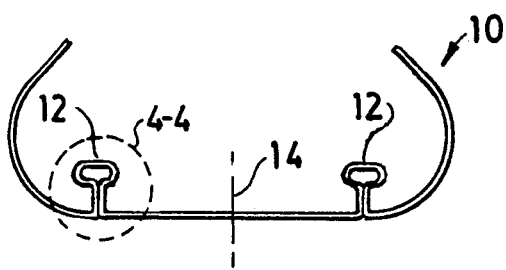
FIG.2
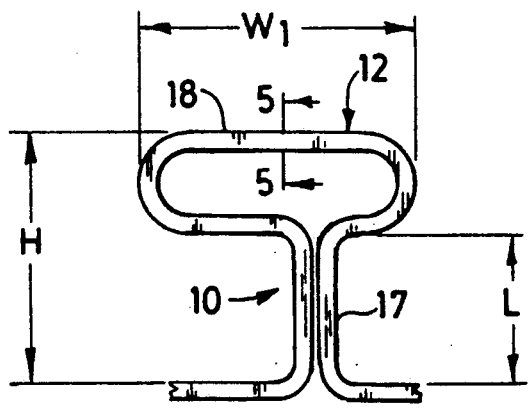
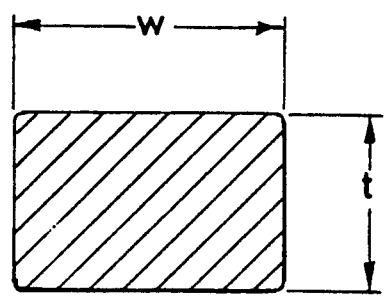
FIG.4          FIG.5

ORTHODONTIC ARCHWIRE

BACKGROUND OF THE INVENTION

The present invention relates generally to appliances used in dentistry and, more particularly, to an orthodontic archwire used in applying corrective forces to maloccluded teeth.

In the practice of orthodontia, various appliances are used to correct the malocclusion of teeth in the mouth of the patient. During this corrective procedure, it is often necessary to impart a variety of forces to the teeth so as to move the teeth to their final desired position. Typically this is achieved through the use of a variety of different appliances, either simultaneously or consecutively. One of the most common appliances used in orthodontics is an orthodontic archwire which is secured to orthodontic brackets which in turn are attached to the teeth of a patient. Typical prior art orthodontic archwires have been limited with respect to the amount of movement that can take place and the type of forces which can be applied. It is often necessary to frequently change the archwire or to use other auxillary-type appliances to move the teeth to their final position. Elastic chains and coil metal springs are used as retraction mechanisms by attaching them in tension between fixed anchor points in the mouth and the tooth desired to be moved. Springs have been built into the archwire itself, however, this is difficult for the orthodontist to fabricate, and requires considerable non-productive time on the part of the orthodontist.

In accordance with the present invention, Applicants have developed an orthodontic archwire which through a unique combination of material properties and shape can be activated for retraction of anterior teeth, provide intrusion of anterior teeth, provide extrusion and bite opening of the posterior section, as well as mesial ligually rotation of posterior teeth simultaneously thereby eliminating or minimizing the need for several wire changes which will reduce the treatment time and provide a cost savings for the doctor by using fewer wires and having to see the patient fewer times.

SUMMARY OF THE INVENTION

In one aspect of the present invention, there is provided an orthodontic appliance having a force-imparting archwire for applying corrective force to a tooth. The archwire has a generally U-shaped configuration with a pair of loop structures disposed therein, one loop structure is disposed on each side of the mesial center line. Each of the loop structures comprise a pair of substantially vertically extending legs placed substantially adjacent each other which form a substantially closed loop section at their upper end. The orthodontic archwire has a central anterior section and a pair of posterior sections extending on either side of the anterior section. The posterior sections of the archwire are shaped so as to have a reverse curvature of spee and toe in curvature.

In another aspect of the present invention, there is provided a method of making an orthodontic archwire made of a titanium molybdenum alloy comprising the steps of:
a) forming a generally U-shaped archwire from a continuous length of wire having a central anterior section and a pair of posterior sections extending from both ends of the anterior section, partially forming a pair of loop structures in the archwire and forming the anterior sections with toe in curvature;
b) completing the forming of the loop structure in the archwire;
c) forming a reverse curvature of spee in the posterior sections.

DETAILED DESCRIPTION OF THE DRAWINGS

Referring to FIG. 1, there is illustrated a top plan view of an orthodontic archwire made in accordance with the present invention;

FIG. 2 is a front elevational view of FIG. 1;

FIG. 3 is a side elevational view of the orthodontic archwire of FIG. 1 as taken along line 3—3;

FIG. 4 is an enlarged view of a portion of the archwire of FIG. 2 taken along line 4—4 illustrating one of the loop structures formed in the archwire;

FIG. 5 is an enlarged cross-sectional view of FIG. 4 taken along line 4—4 illustrating the cross configuration of the archwire;

DETAILED DESCRIPTION OF THE INVENTION

Figure 6:
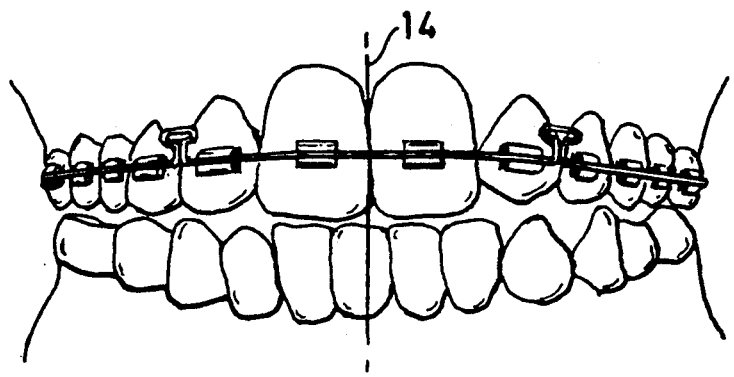
FIG. 6 is a front elevational view of an orthodontic archwire made in accordance with the present invention as placed on the upper jaw of a patient.
Figure 7:
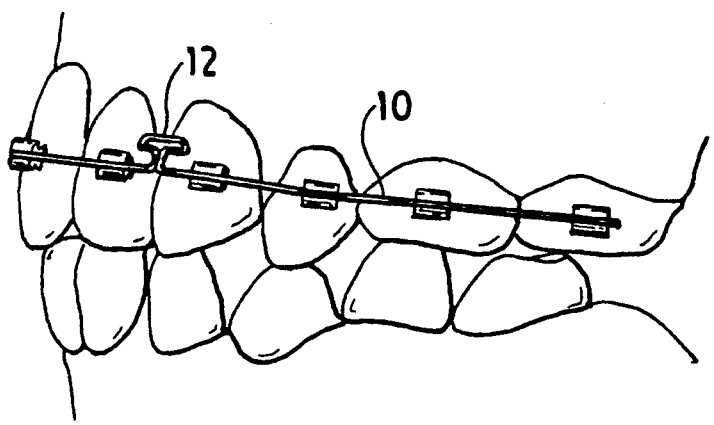
FIG. 7 is a side elevational view of FIG. 6.
Figure 8:
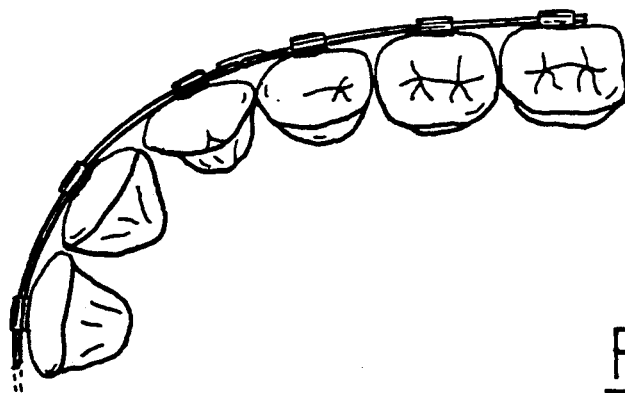
FIG. 8 is a part bottom plan view of the teeth of FIG. 6 as taken along line 8—8.

FIGS. 1–5 and 9, illustrated an orthodontic archwire 10 made in accordance with the present invention, and FIGS. 6–8 illustrate archwire 10 as mounted on the upper teeth of a patient. The orthodontic archwire 10 has a unique configuration and is made of a material having bendability and ductility properties that will enable the orthodontist to perform a variety of different functions and provides a large working range over which orthodontic forces can be maintained. In particular, the archwire 10 is made from a material having a flexural modulus in the range of about 3 to 15 million psi, preferably in the range of 6 to 10 million psi. Applicants have also found that the set angle of the orthodontic archwire should be less than 75°, preferably less than 70° as measured by a Tinius Olsen Bending Machine with ¼ inch span wherein the wire has been subjected to a 90° bend. Applicants have found that an orthodontic wire made out of a titanium molybdenum alloy is capable of providing the desired physical properties. U.S. Pat. No. 4,197,643 disclose some alloys of the general type suitable for the present invention. In order to maintain the appropriate ductility required for an archwire made in accordance with the present invention, the wire should be made of a material having a body centered cubic structure having a maximum of 30% alpha phase form. Applicants have found the following alloy composition to be suitable:

|  | % By Weight |
| --- | --- |
| Mo (Molybelenum) | 11.5% ± 2% |
| Zr (Zirconium) | 6.0% ± 2% |
| Sn (Tin) | 4.5% ± 2% |
| Ti (Titanium) | balance |

The above alloy can be manufactured to provide the following properties: a modulus of elasticity in the range of about 5 to 15 million psi, a set angle of about 70° and a flexural modulus in the range of 6 to 10 million psi.

Figure 4A:
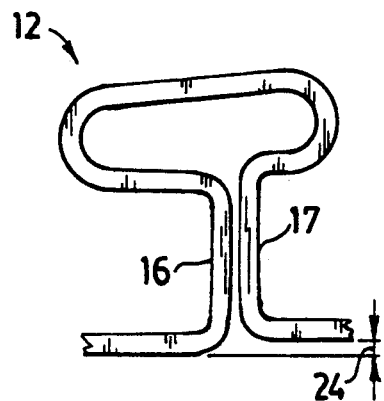
FIG. 4A is a view similar to FIG. 4 illustrating the loop structure having a step formed therein for intrusion of the teeth.
Figure 4B:
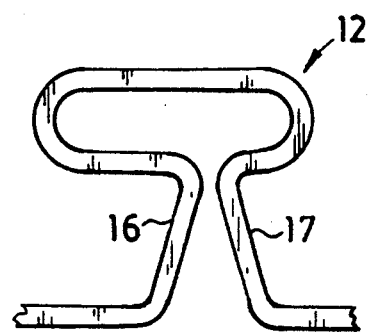
FIG. 4B is a view similar to FIG. 4 illustrating the loop structure activated for providing retraction of the teeth.

The orthodontic archwire 10 is provided with a pair of loop structures 12 which are formed at a point substantially equally distant from the mid line 14 at the apex of the archwire 10. In the preferred embodiment illustrated, loop structures 12 are integrally formed as part of archwire 10 through opposite bending operation integrally formed on the archwire 12, thus, the archwire is a single continuous element without any welds. In the preferred embodiment, the archwire 10 has a substantially rectangular cross sectional shape, having a width W and a thickness T. The thickness T ranging from about 0.016 to 0.019 inches (0.406 mm to 0.48 mm) and W ranges from about 0.022 to 0.025 inches (0.558 mm to 0.635 mm). However, the cross sectional shape and size of archwire 10 may be varied as discussed. In the particular embodiment illustrated, each loop structure 12 comprises a pair of substantially vertically extending legs 16,17 which are preferably placed adjacent each other so that no space is present between legs 16,17. The legs 16,17 form a substantially closed loop section 18 at the upper end. In the particular preferred embodiment, loop structure 12 has a substantially T-shaped configuration. The loop structures 12 each have a height H as measured from the main section of archwire 10. The legs 16,17 having a length L. The height H, width W and length L may be varied to provide the desired force and a width W. While in the preferred embodiment loop structures 12 are substantially T-shaped, it is to be understood that the loop structures 12 may have a variety of other configurations, for example such as P-shaped. What is important with regard to the loop structures 12 is that each loop structure 12 is provided with two vertical legs 16,17 closely adjacent to each other and form some a generally closed loop section 18 spaced from the main body section of the archwire 10, which provides the loop structure with the ability of setting the legs in a position relative to each other as illustrated in FIGS. 4A and 4B to provide the desired forces. The portion of archwire 10 generally between the two loop portions 12 is considered the anterior portion 20 of the orthodontic archwire 10 and the portions extending on either side of the anterior section toward the rear of the orthodontic archwire 10 are typically referred to as the posterior sections of the archwire 10. The particular point at which the anterior and posterior sections 20,22 meet may vary in accordance to that typically found in the prior art. Applicants have found that the anterior section 22 generally ranges from about 22 mm to about 42 mm in the central section of the archwire 10.

As best seen in FIG. 3, the posterior section of orthodontic archwire 10 has a reverse curvature of spee as represented by the radius R. The amount and shape of the reverse curvature of spee is selected in accordance with desired shapes that are well known in the orthodontic field. In the particular embodiment illustrated, the reverse curvature of spee has a radius R, which typically ranges from about 1 to 3 inches (2.54 cm to 7.62 cm). Additionally, the radius R may be a single radius or a compound radius as desired by the orthodontist. The reverse curve of spee provides forces which result in extrusion of teeth and bite opening.

For intrusion of the teeth, a step 24 may be placed in the anterior section 20 of the archwire 10 with respect to the loop structure 12 as illustrated in FIG. 4A. Typically, the size of step 24 ranges between 1 and 3 mm. However, the step 24 may be provided as large or small as desired and may be placed at a point appropriate for providing the desired amount of intrusion.

The T loop structures 12 can also be activated for retraction of the anterior teeth. This is accomplished by separating the legs 16 of the loop structure 12 in a mesial distal direction as shown in FIG. 4B. The loop structure in FIG. 4B having a generally reverse V-shaped configuration.

Figure 9:
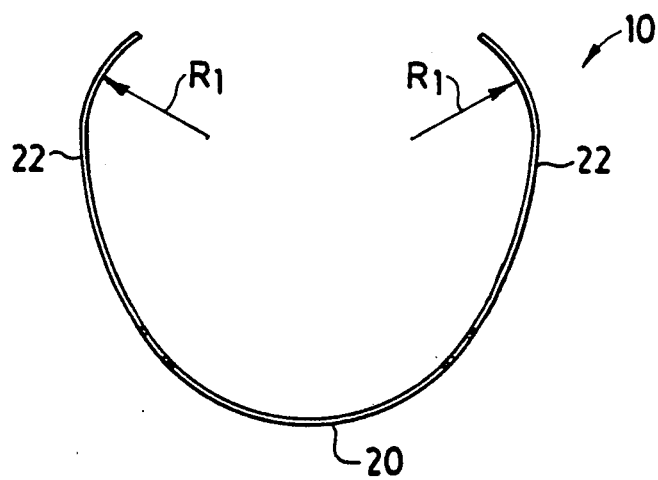
FIG. 9 is a top plan view of the archwire of figure after initial formation of the loop structures but before forming the reverse curvature of spee in the posterior section.

As is best seen in FIG. 1 and 9, the posterior sections of archwire 10 are curved inwardly (toed in), each having a radius $R_1$. The radius $R_1$ is preferably in the range of 1.0 inches to about 1.5 inches (2.54 cm to 3.81 cm). Preferably, as is also illustrated, radius $R_1$ is a compound curve with the smaller radius being located at the outer end of the posterior section of archwire 10. The toed in configuration provides for the mesial ligual rotation of molar teeth.

The orthodontic archwire 10 can be used to provide several separate functions which were required to be performed independently and typically at different times. The material properties of the archwire 10 are selected such that various forces can be applied to the teeth at the same time and over substantial distances. The present invention allows various orthodontic procedures to occur simultaneously and more efficiently over large working distances, thus reducing the treatment time and provide a cost savings for the doctor by using fewer wires and having to see the patient fewer times. In testing of archwires made in accordance with the present invention, the number of wire changes have averaged 50% less than typical prior art procedures, and time periods for the procedures have been reduced approximately 60%.

The orthodontic archwire 10 is made by first selecting the desired raw material having the desired physical, chemical and mechanical properties. For example; by taking a length of straight wire 30 having a rectangular cross section made from a material having the desired characteristics. Archwire 10 with loop structures are made from a continuous length of wire which is wrapped around a spool having a predetermined diameter. In the manufacture of archwire 10, a 6 inch (15.24 cm) diameter spool is used; however, a diameter as low as 3 inches (9.62 cm) has been found suitable.

The manufacturing process involves the partial formation of the loops structure 12, the anterior and posterior curvatures, followed by a secondary operation which will finish the loop formation as well as completing the general U-shaped/horseshoe shaped arch form. In the final operation the reverse curves of spee are formed.

It is important that no residual torque be present in the archwire. Applicants have found that forming the archwire with a Torin spring mandrel or a four slide apparatus provides an archwire without any subustantial residual torque.

It is to be understood that various changes and modifications may be made without departing from the scope of the present invention. The present invention being defined by the following claims.

What is claimed is:

1. In an orthodontic appliance having a force-imparting archwire for applying corrective force to a tooth, said archwire having a generally U-shaped configuration having a central anterior section and a pair of posterior sections extending on either side of said anterior section, a pair of T-loop structures formed in said archwire, one of said T-loop structures being disposed on each side of said mesial center line, each of said T-loop structure comprising a pair of substantially vertically extending legs placed substantially adjacent each other which form a substantially closed loop section at their upper end, said posterior sections of said archwire each having a reverse curvature of spee of a first predetermined radius and a toe is curvature of a second predetermined radius.

2. The orthodontic appliance of claim 1 wherein said first predetermined radius ranges from 1 to 3 inches and said second predetermined radius ranges from 1 to 1.5 inches.

3. The orthodontic appliance of claim 1 wherein said reverse curvature of spee and said toe in curvature have a compound radius.

4. The orthodontic appliance of claim 1 wherein said loop structures are located at a distance from the mesial distal center line in the range of 22 to 42 mm.

5. The orthodontic appliance of claim 1 wherein said archwire is made of material having a modulus of elasticity in the range of about 8 million to about 12 million psi.

6. The orthodontic appliance of claim 1 wherein said reverse curvature of spee of said posterior section is in the range of 1 to 3 inches (2.54 cm to 7.62 cm).

7. The orthodontic appliance of claim 1 wherein said archwire is made of a titanium molybdenum alloy having a body centered cubic structure having a maximum 30% alpha phase.

8. The orthodontic appliance according to claim 7 wherein said alloy has the following composition:

| | |
|---|---|
| Mo | 11.5% ± 2% |
| Zr | 6.0% ± 2% |
| Sn | 4.5% ± 2% |
| Ti | balance |

9. The orthodontic appliance according to claim 1 wherein said archwire has a set angle less than about 75°.

10. The orthodontic appliance according to claim 1 wherein said archwire has a set angle less than about 70°.

11. The orthodontic appliance according to claim 1 wherein said orthodontic archwire has a substantially rectangular cross-sectional configuration.

12. The orthodontic appliance according to claim 11 wherein said archwire is made from a material having a flexural modulus in the range of 5 to 15 million psi and a set angle less than about 75°.

13. The orthodontic appliance according to claim 12 wherein said flexural modulus is in the range of 6 to 10 million psi and the set angel is less than about 70°.

14. The orthodontic appliance according to claim 11 wherein said orthodontic archwire has a thickness in the range of about 0.016 to 0.019 inches and a width in the range of about 0.022 to 0.025 inches.

15. The method of making an orthodontic archwire having the desired physical characteristics comprising the steps of:
   a) forming a generally U-shaped archwire from a continuous length of wire having a central anterior section and a pair of posterior sections extending from both ends of said anterior section, partially forming a pair of loop structures in said archwire and forming said anterior sections with toe in curvature;
   b) completing the forming of said loop structure in said archwire
   c) forming a reverse curvature of spee in the posterior sections.

16. In an orthodontic appliance having a force-imparting archwire for applying corrective force to a tooth, said archwire having a generally U-shaped configuration having a central anterior section and a pair of posterior sections extending on either side of said anterior section; a pair of loop structures formed therein, one of said loop structures being disposed on each side of said mesial center line, each of said loop structure comprising a pair of substantially vertically extending legs placed substantially adjacent each other which form a substantially closed loop section at their upper end, said posterior sections of said archwire each having the reverse curvature of spee of a first predetermined radius and a toe in curvature of a second predetermined radius, said archwire being made of a material having a flexural modulus between 3 to 15 million psi.

17. The orthodontic bracket according to claim 16 wherein said archwire is made of a titanium molybdenum alloy having a body centered cubic structure having a maximum 30% alpha phase.

18. The orthodontic appliance of claim 16 wherein said first predetermined radius ranges from 1 to 3 inches and said second predetermined radius ranges from 1 to 1.5 inches.

19. The orthodontic appliance of claim 16 wherein said reverse curvature of spee and said toe in curvature have compound radius.

20. The orthodontic appliance of claim 16 wherein said loop structures are located at a distance from the mesial distal center line in the range of 22 to 42 mm.

21. The orthodontic appliance of claim 16 wherein said archwire is made of material having a modulus of elasticity in the rang of about 8 million to about 12 million psi.

22. The orthodontic appliance of claim 16 wherein said reverse curvature of spee of said posterior section is in the range of 1 to 3 inches (2.54 cm to 7.62 cm).

23. The orthodontic appliance of claim 16 wherein said archwire is made of a titanium molybdenum alloy having a body centered cubic structure having a maximum 30% alpha phase.

24. An orthodontic appliance according to claim 23 wherein said alloy has the following composition:

| | |
|---|---|
| Mo | 11.5% ± 2% |
| Zr | 6.0% ± 2% |
| Sn | 4.5% ± 2% |
| Ti | balance |

25. The orthodontic appliance according to claim 16 wherein said archwire has a set angle less than about 75°.

26. The orthodontic appliance according to claim 16 wherein said archwire has a set angle less than about 70°.

27. The orthodontic appliance according to claim 16 wherein said orthodontic archwire has a substantially rectangular cross-sectional configuration.

28. The orthodontic appliance according to claim 27 wherein said archwire is made from a material having a flexural modulus in the range of 5 to 15 million psi and a set angle less than about 75.

29. The orthodontic appliance according to claim 28 wherein said flexural modulus is in the range of 6 to 10 million psi and the set angle is less than about 70°.

* * * * *

UNITED STATES PATENT AND TRADEMARK OFFICE
CERTIFICATE OF CORRECTION

PATENT NO. : 5,131,843
DATED : July 21, 1992
INVENTOR(S) : James J. Hilgers et al.

It is certified that error appears in the above-identified patent and that said Letters Patent is hereby corrected as shown below:

Column 5, line 19, "is" should be --in--.

Column 5, line 43, "The" should be --An--.

Column 5, line 66, "angel" should be --angle--.

Column 6, line 48, "rang" should be --range--.

Column 8, line 3, insert --°-- after "75" and before the period.

In the Abstract, line 7, delete "," after "form.".

Signed and Sealed this

Seventh Day of December, 1993

*Attest:*

BRUCE LEHMAN

*Attesting Officer*     *Commissioner of Patents and Trademarks*